United States Patent
Wisda

(10) Patent No.: US 12,426,831 B1
(45) Date of Patent: Sep. 30, 2025

(54) METHODS FOR INDUCING SLEEP, CONTROLLING BRAIN WAVE FREQUENCY, AND/OR CONTROLLING HEART RATE USING MUSIC

(71) Applicant: Bryan Wisda, Carefree, AZ (US)

(72) Inventor: Bryan Wisda, Carefree, AZ (US)

( * ) Notice: Subject to any disclaimer, the term of this patent is extended or adjusted under 35 U.S.C. 154(b) by 1390 days.

(21) Appl. No.: 16/774,668

(22) Filed: Jan. 28, 2020

Related U.S. Application Data

(60) Provisional application No. 62/800,421, filed on Feb. 1, 2019.

(51) Int. Cl.
*A61B 5/00* (2006.01)
*A61B 5/024* (2006.01)
*A61B 5/24* (2021.01)
*A61M 21/00* (2006.01)

(52) U.S. Cl.
CPC ............ *A61B 5/4806* (2013.01); *A61B 5/024* (2013.01); *A61B 5/24* (2021.01); *A61B 5/6898* (2013.01); *A61M 21/00* (2013.01)

(58) Field of Classification Search
CPC ......... A61B 5/4806; A61B 5/024; A61B 5/24; A61B 5/6898; A61M 21/00
USPC ...................................................... 600/26–28
See application file for complete search history.

(56) References Cited

U.S. PATENT DOCUMENTS

| | | | | |
|---|---|---|---|---|
| 2007/0203421 A1* | 8/2007 | Cho | ....................... | A61B 5/486 600/519 |
| 2010/0056854 A1* | 3/2010 | Chang | .................. | A61M 21/00 600/28 |
| 2013/0177883 A1* | 7/2013 | Barnehama | .............. | G09B 7/00 434/236 |
| 2013/0234823 A1* | 9/2013 | Kahn | ..................... | A61B 5/369 340/3.1 |
| 2014/0343354 A1* | 11/2014 | Larson | ................. | A61B 5/4812 600/28 |
| 2016/0008568 A1* | 1/2016 | Attia | ...................... | A61B 5/486 600/28 |
| 2016/0055842 A1* | 2/2016 | DeFranks | ............ | G10K 11/175 381/66 |
| 2016/0302718 A1* | 10/2016 | Laura Lapoint | ....... | A61B 5/375 |
| 2017/0173296 A1* | 6/2017 | Park | ..................... | A61B 5/4836 |
| 2017/0286536 A1* | 10/2017 | Rando | ............. | H04N 21/42201 |
| 2018/0250494 A1* | 9/2018 | Hanbury | ............. | A61B 5/6803 |
| 2019/0282779 A1* | 9/2019 | Holloway | ............. | A61M 21/02 |
| 2020/0000348 A1* | 1/2020 | Bartosch | ................ | A61B 5/024 |

(Continued)

OTHER PUBLICATIONS

Imeraj L, Antrop I, Roeyers H, Deschepper E, Bal S, Deboutte D. Diurnal variations in arousal: a naturalistic heart rate study in children with ADHD. Eur Child Adolesc Psychiatry. Aug. 2011;20(8):381-92. doi: 10.1007/s00787-011-0188-y. Epub May 29, 2011. PMID: 21626226. (Year: 2011).*

(Continued)

*Primary Examiner* — Sunita Reddy
(74) *Attorney, Agent, or Firm* — IPTechLaw

(57) ABSTRACT

Implementations of a method of inducing a desired physiological state may include playing a song including a binaural frequency using an audio playback device and synchronizing one or more brain wave frequencies of a listener to the binaural frequency of the song. The binaural frequency of the song may include a binaural beat, a heart rate rhythm, and a mental target frequency.

11 Claims, 10 Drawing Sheets

(56) References Cited

U.S. PATENT DOCUMENTS

2021/0178112 A1* 6/2021 Ning ................. G16H 20/30

OTHER PUBLICATIONS

Ostchega Y, Porter KS, Hughes J, Dillon CF, Nwankwo T. Resting pulse rate reference data for children, adolescents, and adults: United States, 1999-2008. Natl Health Stat Report. Aug. 24, 2011;(41):1-16. PMID: 21905522. (Year: 2011).*

Adhdlullaby by Brian Wisda, 2018 (see attached) (Year: 2018).*

Dictionary Definition of Homeostasis, Source:Webster's New World College Dictionary, 4th Edition. Copyright © 2010 by Houghton Mifflin Harcourt, accessible at https://www.collinsdictionary.com/us/dictionary/english/homeostasis (Year: 2010).*

Awake Technologies, Binaural Beats—Sounds That Change Brainwaves? Do They Actually Work?, Retrieved from the Internet: http://www.breakthroughpsychologyprogram.com/binaural-beats.html, downloaded on Jan. 30, 2019, 65 pages.

Mitchum, R., Groove is in the Heart: Matching Bests Per Minute to Heart Rate, Retrieved from the Internet: https://medium.com/@Spotify/groove-is-in-the-heart-matching-beats-per-minute-to-heart-rate-271a79b7f96a, Nov. 1, 2016, 8 pages.

Armon, R., et al., Effects of Music Tempos on Blood Pressure, Heart Rate, and Skin Conductance After Physical Exertion, University of Wisconsin—Madison, Jan. 2011, 12 pages.

Fleming, S., et al., Normal Ranges of Heart Rate and Respiratory Rate in Children from Birth to 18 Years: A Systematic Review of Observational Studies, Lancet., 377 (977), Mar. 19, 2011, 16 pages.

Herrmann, N., What is the Function of the Various Brainwaves?, Scientific American, Dec. 22, 1997, 5 pages.

Wikipedia, OODA Loop, Retrieved from the Internet: https://en.wikipedia.org/w/index.php?title=OODA_loop&oldid=87712760"2, downloaded on Jan. 30, 2019, 4 pages.

Boyd, J., OODA LOOP: What You Can Learn from Fighter Pilots About Making Fast and Accurate Decisions, Retrieved from the Internet: fs.blog/2018/01/john-boyd-ooda-loop, Jan. 21, 2018, 8 pages.

Binaural Beats Meditation, 432 Hz—Unearthing the Truth Behind Nature's Frequency, Retrieved from the Internet: https://www.binauralbeatsmeditation.com/432-hz-truth-behind-natures-frequency/, downloaded on Jan. 30, 2019, 6 pages, Apr. 18, 2016 (source: Internet Archive (Wayback machine,https://archive.org/web/).

* cited by examiner

METHODS FOR INDUCING SLEEP, CONTROLLING BRAIN WAVE FREQUENCY, AND/OR CONTROLLING HEART RATE USING MUSIC

CROSS REFERENCE TO RELATED APPLICATIONS

This document claims the benefit of the filing date of U.S. Provisional Patent Application 62/800,421, entitled "Methods for Inducing Sleep, Controlling Brain Wave Frequency, and/or Controlling Heart Rate Using Music" to Bryan Wisda which was filed on Feb. 1, 2019, the disclosure of which is hereby incorporated entirely herein by reference.

BACKGROUND

1. Technical Field

Aspects of this document relate generally to inducing a physiological state. More specific implementations involve inducing sleep, assisting the listener with gaining focus, relaxing, or preparing mentally.

2. Background

The human brain operates using various electrical waves which include gamma, beta, alpha, theta, and delta waves. The human brain controls various physical systems via the central nervous system where the brain influences/controls body functions and operation under the conscious and unconscious direction of the person.

SUMMARY

Implementations of a method of inducing a desired physiological state may include playing a song including a binaural frequency using an audio playback device and synchronizing one or more brain wave frequencies of a listener to the binaural frequency of the song. The binaural frequency of the song may include a binaural beat, a heart rate rhythm, and a mental target frequency.

Implementations of a method of inducing a desired physiological state may include one, all, or any of the following:

A desired physiological state may be induced using the synchronizing of the one or more brain wave frequencies of the listener.

The mental target frequency may be 432 Hz.

An auditory progression may be generated and included within the song.

The song may be included within a compilation of songs, and each song of the compilation of songs may include a binaural frequency.

Each song of the compilation of songs may include a different binaural frequency.

Implementations of a method of generating a binaural frequency may include selecting a target heart rate, selecting a target brain wave frequency of one or more brain wave frequencies of a listener, and generating an auditory progression. The auditory progression may be configured to adjust a heart rate of a listener from a homeostatic heart rate to the target heart rate and a brain wave frequency of the listener from a homeostatic brain wave frequency to the target brain wave frequency.

Implementations of a method of generating a binaural frequency may include one, all, or any of the following:

The method may include adjusting the heart rate of the listener up to the target heart rate, and adjusting the brain wave frequency of the listener up to the target brain wave frequency, using the auditory progression.

The method may also include adjusting the heart rate of the listener down to the target heart rate and adjusting the brain wave frequency of the listener down to the target brain wave frequency, using the auditory progression.

The method may also include adjusting the heart rate of the listener up and down to the target heart rate and adjusting the brain wave frequency of the listener up and down to the target brain wave frequency, using the auditory progression.

The method may include inducing a desired physiological state using the auditory progression.

The auditory progression may be included within a song.

The auditory progression may be included within a progression of songs.

The target brain wave frequency may be 432 Hz.

Implementations of a method of generating a binaural frequency may include selecting a target heart rate, selecting a target brain wave frequency of one or more brain wave frequencies of a listener, and generating an auditory progression. The auditory progression may be configured to adjust a heart rate of a listener downward, from a homeostatic heart rate to the target heart rate, and to adjust a brain wave frequency of the listener downward, from a homeostatic brain wave frequency to the target brain wave frequency.

Implementations of a method of generating a binaural frequency may include one, all, or any of the following: The method may include inducing a desired physiological state using the auditory progression.

The auditory progression may be included within a song.

The target brain wave frequency may be 432 Hz.

The method may include adjusting the heart rate of the listener in increments of 4 beats per minute until the target heart rate is reached, using the auditory progression of the binaural frequency.

The method may include adjusting the brain wave frequency of the listener in increments of 1 Hz until the target brain wave frequency is reached, using the auditory progression of the binaural frequency.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components, assembly procedures or method elements disclosed herein. Many additional components, assembly procedures and/or method elements known in the art consistent with the intended methods for inducing a desired physiological state will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such methods, and implementing components and methods, consistent with the intended operation and methods.

Figure 1:
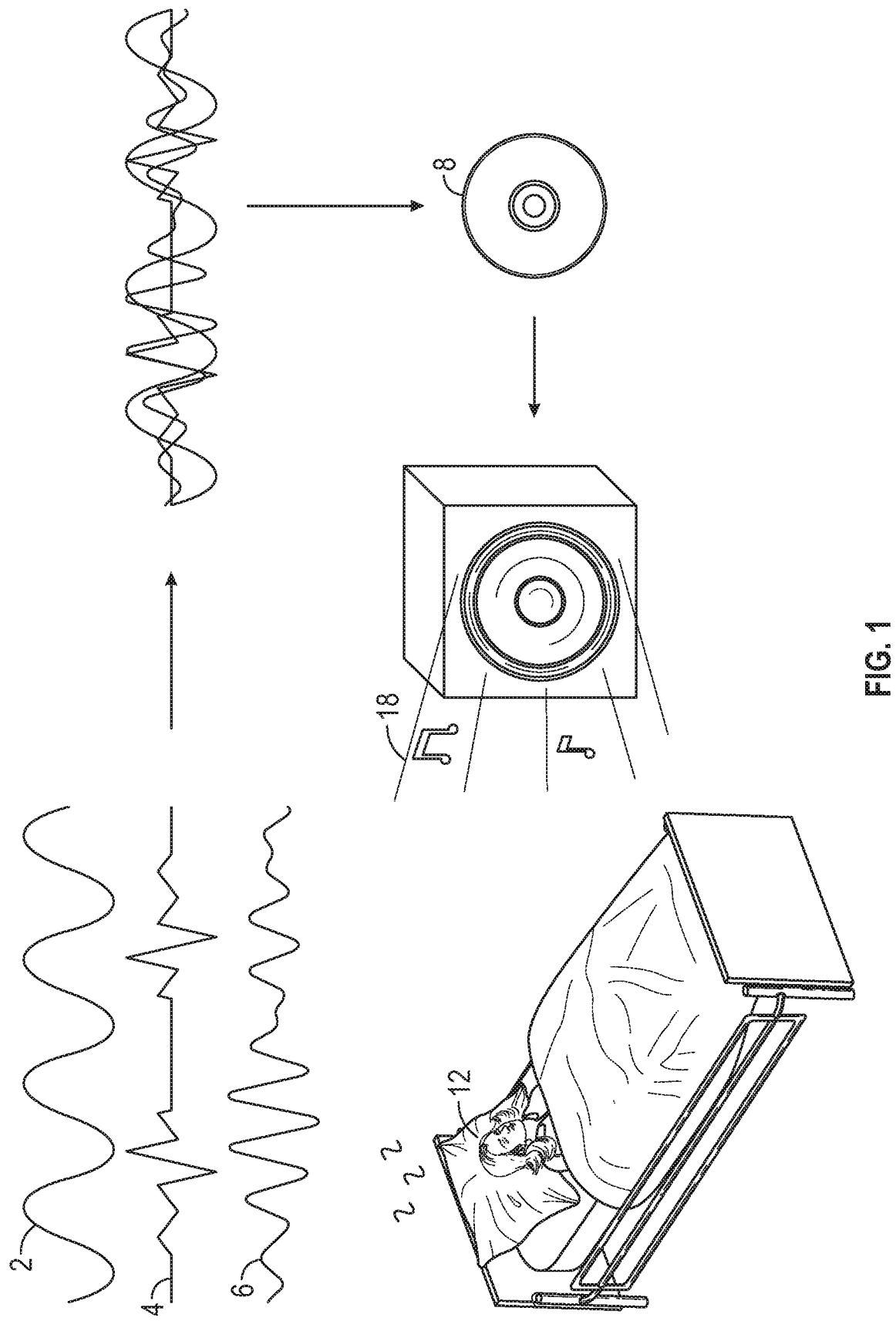
FIG. 1 is a diagram of an implementation of a system for inducing sleep, controlling brain wave frequency, and controlling heart rate using music.

Referring to FIG. 1, a diagram of an implementation of a system for inducing sleep, controlling brain wave frequency, and controlling heart rate using music is illustrated. As illustrated, a binaural beat 2, a target heart rate 4, and a target brain wave frequency 6 are compiled and embedded within a song. As part of the method, a number of songs is prepared to be played to a user in a specified sequence. Each song includes respective musical components designed to assimilate/engage/align a listener's brain waves and heart rate to induce a particular desired mental state. The musical components of each song may include a heart rate rhythm, a binaural beat, a mental target frequency, and rhythmic and non-rhythmic elements. More specifically, the heart rate rhythm is used to sync the heart rate of the listener to the rhythm of the song, and thus to align the listener's heart rate to the overall heart rate rhythm progression of the compilation of songs as each song is heard by the user in the specified sequence. A binaural beat is used along with the heart rate rhythm to simulate brain wave frequencies and to synchronize the brain wave frequency of the listener to the binaural frequency of the song and to the overall binaural frequency progression of the compilation of songs. The song is then burned onto, or stored within, a compact disc (CD) 8. As illustrated, when the music 10 from the CD 8 is played for a listener 12, the listener 12 may be induced to fall asleep.

Figure 2:
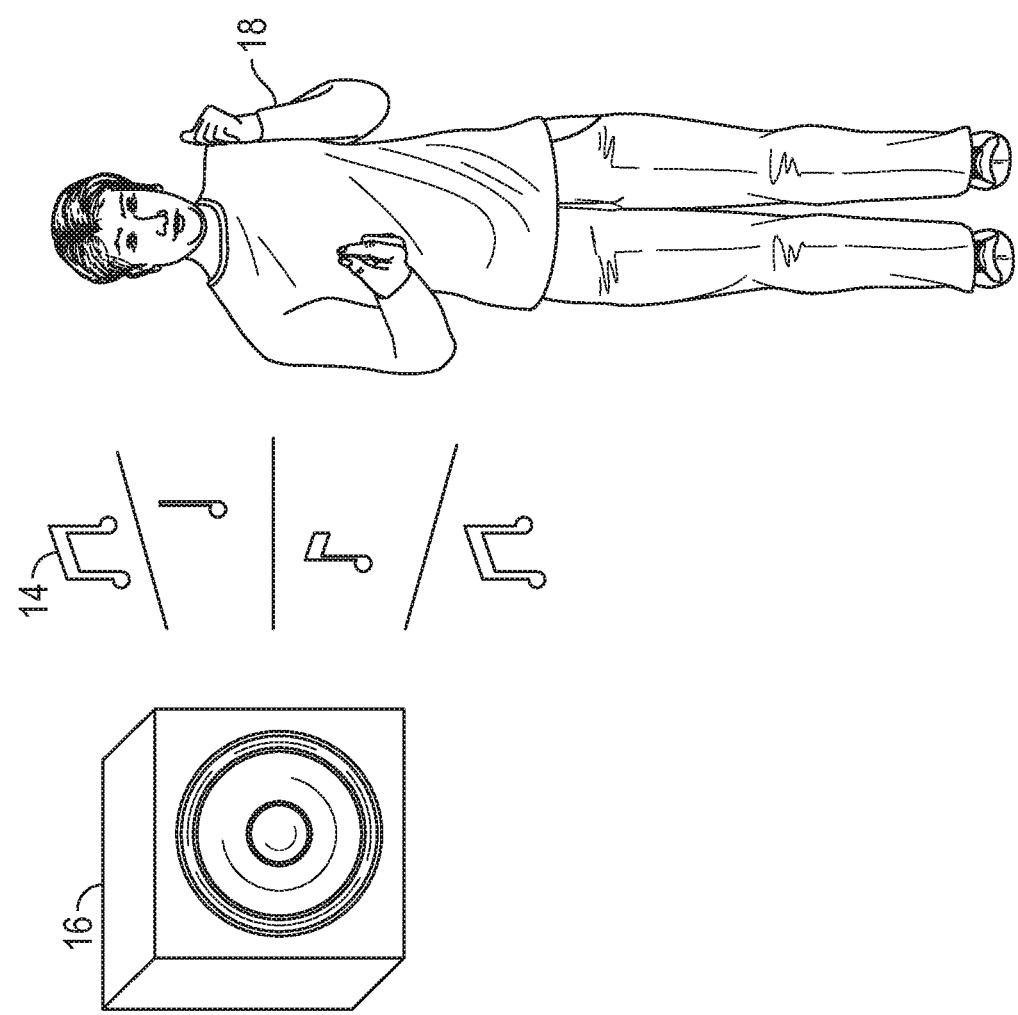
FIG. 2 is a diagram of an implementation of a system for inducing a desired physiological state, controlling brain wave frequency, and controlling heart rate using music.

Referring to FIG. 2, a diagram of an implementation of a system for inducing a desired physiological state, controlling brain wave frequency, and controlling heart rate using music is illustrated. As illustrated, music 14 is played via a speaker 16, for a listener 18. The embedded binaural frequency within the music 14, or song, induces the desired physiological state of the listener 18. As the listener is exposed to the music of the song, the listener's brain processes the music of the song and works with the central nervous system of the listener. As a result, the listener of the song or compilation of songs has their heart rate assimilate/align with the rhythm of the music of each song over the time period each song lasts. When listened to in a predetermined progression, the heart rate of the listener steps down or steps up in line with the parameters of each song. In various implementations, each song in the set of songs of the music may have a steady/consistent rhythm from song to song or a consistently increasing or decreasing rhythm from song to song. In various implementations, each song in the set of songs may also have changing binaural beats song to song or a constant binaural beat song to song, in order to achieve this gradual assimilation.

Figure 3:
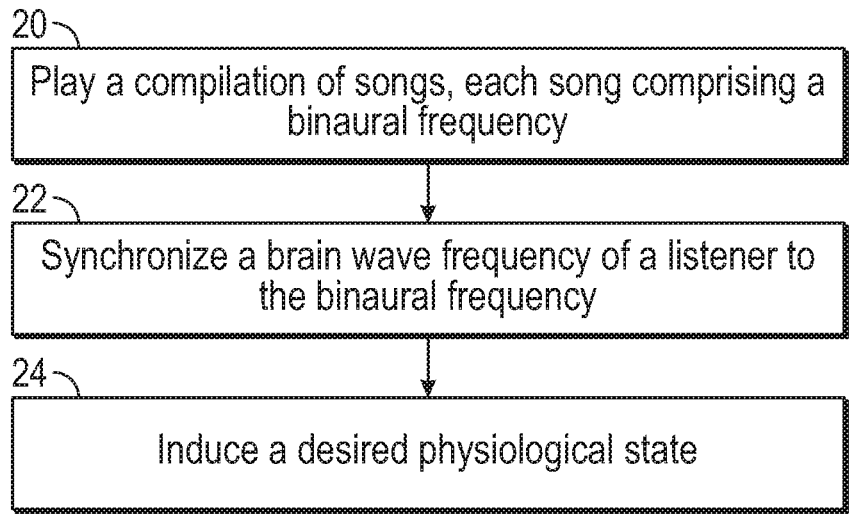
FIG. 3 is a flow chart of an implementation of a method of inducing a desired physiological state.

Referring to FIG. 3, a flow chart of an implementation of a method of inducing a desired physiological state is illustrated. As illustrated, a compilation of songs is played 20. Each song within the compilation of songs includes a binaural frequency. Next, as a result of receiving and processing the binaural frequency, the listener's brain synchronizes a brain wave frequency of the listener to the binaural frequency 22. Lastly, and as a result of the brain wave frequency synchronization, the brain then interacts with the central nervous system of the listener substantially unconsciously to induce a desired physiological state 24 in the user. In various implementations, the desired physiological state may be sleep. In other implementations, the desired physiological state may be an excited or otherwise aroused state to aid the listener to participate in a desired activity, such as, by non-limiting example, a sports game, an exercise program, or any other activity where the particular physiological state gives a desired effect.

Figure 4:
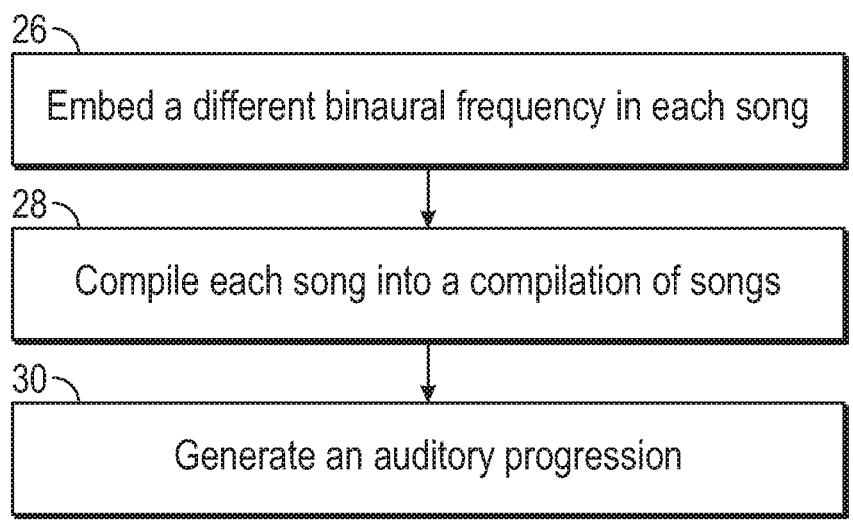
FIG. 4 is a flow chart of an implementation of a method of generating an auditory progression.

Referring to FIG. 4, a flow chart of an implementation of a method of generating an auditory progression is illustrated. As illustrated, a different binaural frequency is embedded into each song 26. The process of embedding refers to an audio mixing process that adds the binaural frequency to one or more additional frequencies included in the song. Following embedding of the binaural frequency into the song, each song is compiled into a compilation of songs 28. With the compilation of songs, the method includes generating an auditory progression 30 through determining a sequence of the songs.

Figure 5:
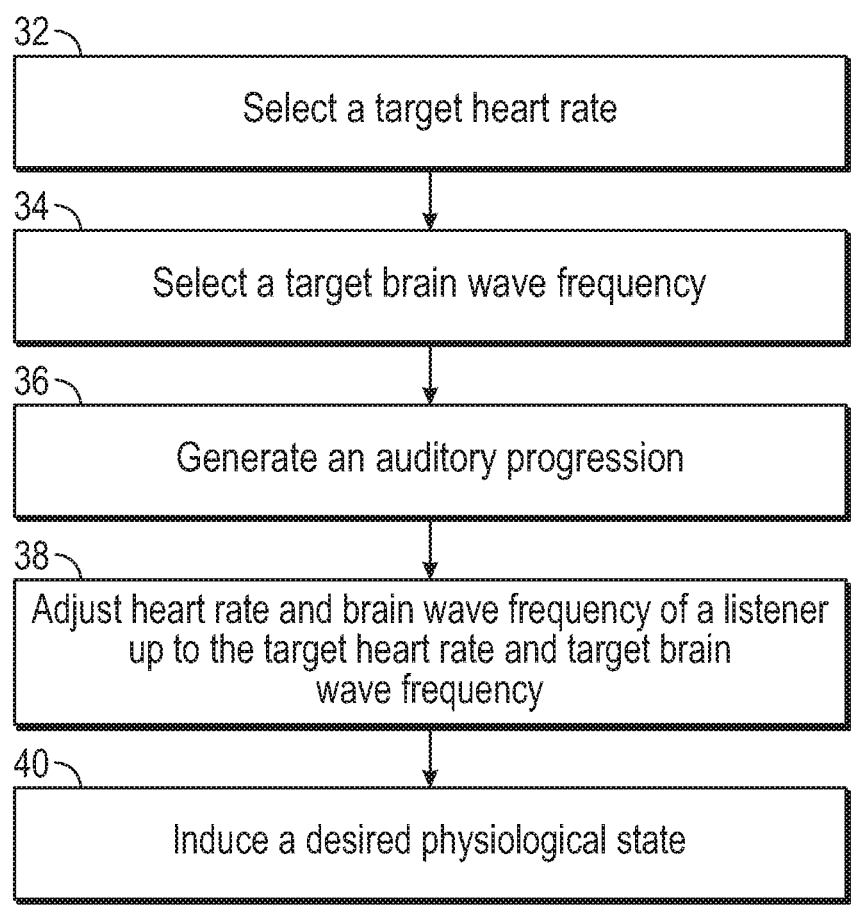
FIG. 5 is a flow chart of an implementation of a method of inducing a desired physiological state, using the auditory progression to adjust a target heart rate and target brain wave frequency upward.

Referring to FIG. 5, a flow chart of an implementation of a method of inducing a desired physiological state, using an auditory progression to adjust a target heart rate and target brain wave frequency upward is illustrated. As illustrated, a target heart rate is selected 32. A target brain wave frequency is also selected 34. An auditory progression is then generated 36 to be in line with/align with/generate/induce the selected target heart rate and target brain wave frequency when the auditory progression is processed by the listener's brain. Next, the heart rate and brain wave frequency of a listener are adjusted up to the target values 38 as the listener's brain processes the auditory progression of the songs and interacts with the central nervous system of the user substantially unconsciously. As a result of the processing of the auditory progression of the songs by the user's brain, a desired physiological state of the listener is induced 40.

Figure 6:
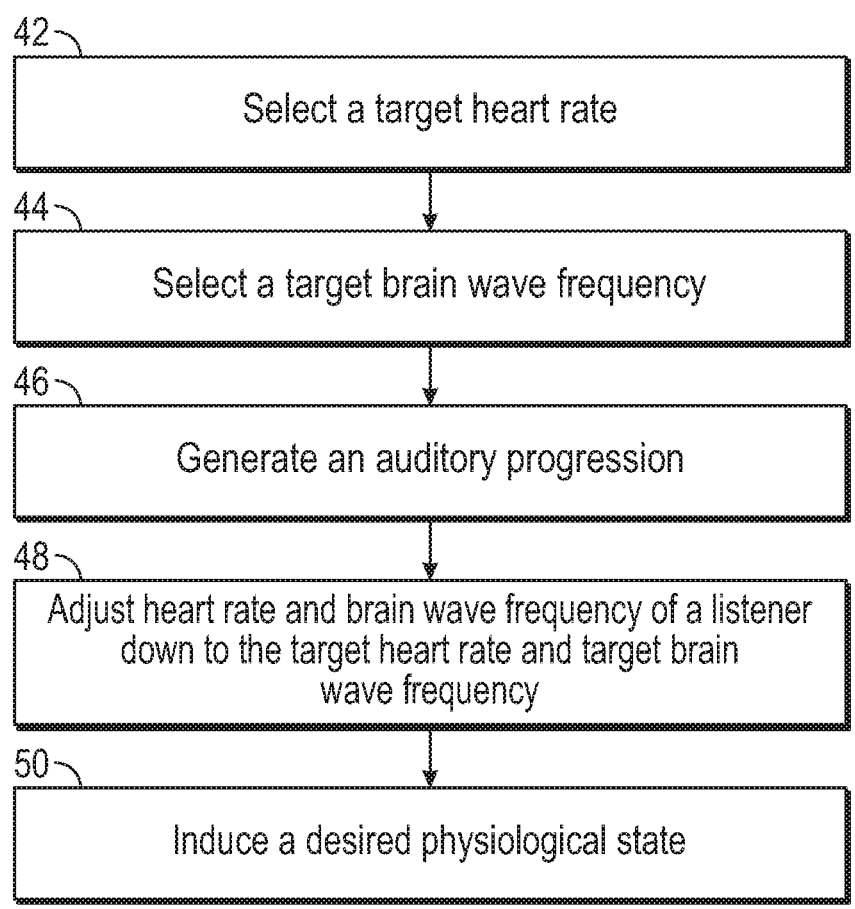
FIG. 6 is a flow chart of an implementation of a method of inducing a desired physiological state, using the auditory progression to adjust a target heart rate and target brain wave frequency downward.

Referring to FIG. 6, a flow chart illustrates an implementation of a method of inducing a desired physiological state, using the auditory progression to adjust a target heart rate and target brain wave frequency downward. As illustrated, a target heart rate is selected 42. A target brain wave frequency is also selected 44. Following selection of the target heart rate and target brain wave frequency (though these could be selected in any order), an auditory progression is generated 46 to be in line with the selected target heart rate and target brain wave frequency. As the auditory progression is implemented in one or more songs played to a listener, the listener's brain processes the auditory progression and interacts with the central nervous system of the listener to adjust the listener's heart rate and brain wave frequency down to the target values 48. Lastly, and as a result of the processing by the listener's brain, a desired physiological state of the listener is induced 50.

In various implementations of a method for inducing sleep, a method of controlling brain wave frequency, and/or a method of controlling heart rate the various methods may include various steps. As illustrated, a target mental state is selected. In various implementations, the target mental state may be sleep, focus, relaxation, meditation, exercise, game performance readiness, or another desired mental state. An age group for which the compilation of songs will be constructed may also be determined, as the musical or other components of the songs or compilation of songs may differ based on the age of the listener. In particular implementations, the compilation of songs may include a compilation of songs targeted towards achieving a sleep state for children ages 8-11. Also the particular mental condition of the audience may be considered as a factor for selecting the musical or other components of the songs or compilation of songs as a compilation may be created to help individuals with, by non-limiting example, attention deficit hyperactivity disorder (ADHD) or another mental or emotional condition(s). Next, with state and/or mental condition determinations made, the desired target heart rate and target brain wave frequency are determined.

In various implementations, the target heart rate may be determined by utilizing the average heart rate for the age group selected, based on the desired mental state at the end of the progression of songs (or goal), such a sleep, focus, performance readiness, or another desired mental state. In one such method implementation, the average sleeping heart rate for 8-11 year olds is 75.6 bpm. In other implementations, the average heart rate for a target age group/functional group (football players, stage performers, etc.) may be determined and applied to the compilation of songs. In one such implementation, the average target brain wave frequency for an 8-11 year old child is approximately 3 Hz.

With the targeted age group/functional group in mind, the homeostatic heart rate and brain wave frequency may be determined. Determining the homeostatic heart rate and/or brain wave frequency(ies) desired may be conducted before or after determining the average heart rate desired in various implementations. In various implementations, the homeostatic heart rate value and brain wave frequency value(s) can be further defined to accommodate a more particular targeted group, such as children of a certain age, who also have Attention Deficit Hyperactivity Disorder (ADHD). Children with ADHD may function at a different homeostatic brain wave frequency than children of the same age who do not have ADHD. In various implementations, the homeostatic brain wave frequency for the targeted group may be dependent on that neuroscientific research available, which will help to specify the homeostatic heart rate and brain wave frequency for a targeted group.

Figure 7:
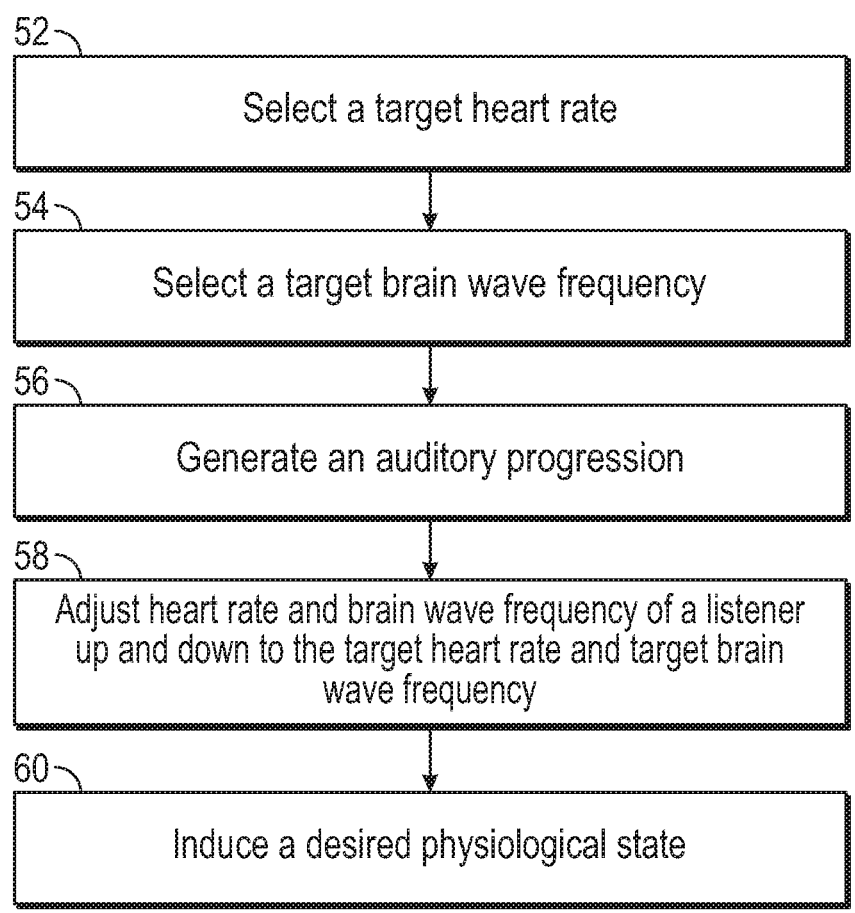
FIG. 7 is a flow chart of an implementation of a method of inducing a desired physiological state, using the auditory progression to adjust a target heart rate and target brain wave frequency upward and downward.

Referring to FIG. 7, a flow chart of an implementation of a method of inducing a desired physiological state, using the auditory progression to adjust a target heart rate and target brain wave frequency upward and downward is illustrated. As illustrated, a target heart rate is selected 52. A target brain wave frequency is also selected 54. An auditory progression is then generated 56 to be in line with the selected target heart rate and target brain wave frequency. The listener's brain then is exposed to the auditory progression through hearing the auditory progression included in one or more songs and processes the auditory progression, interacting with the listener's central nervous system. Substantially autonomously, the heart rate and brain wave frequency of a listener are then adjusted up and down to the target values 58 through the processing by the listener's brain. Through the adjustment of the heart rate and brain wave frequency (ies) adjustment, a desired physiological state of the listener is induced 60.

Figure 8:
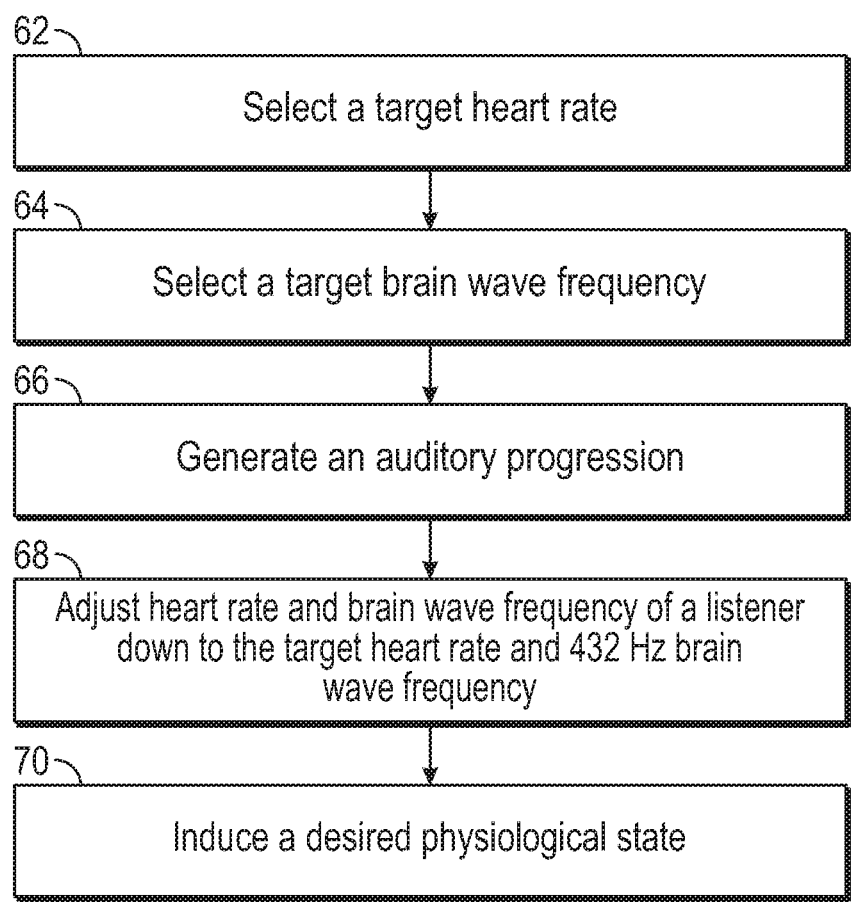
FIG. 8 is a flow chart of an implementation of a method of inducing a desired physiological state, using the auditory progression to adjust a target heart rate and target brain wave frequency of 432 Hz.

Referring to FIG. 8, a flow chart of an implementation of a method of inducing a desired physiological state using the auditory progression to adjust a target heart rate and target brain wave frequency of about 432 Hz is illustrated. As illustrated, a target heart rate is selected 62. A target brain wave frequency is selected 64 of about 432 Hz in this particular implementation. An auditory progression is generated 66 to be in line with the selected target heart rate and target brain wave frequency. Through exposing the listener to the auditory progression through playing one or more songs that include the auditory progression, the heart rate and brain wave frequency of a listener are adjusted to the target values through processing by the user's brain and interaction with the listener's central nervous system, with the target brain wave frequency being 432 Hz 68. A brain wave frequency progression may also be calculated in various implementations. In one implementation of a brain wave frequency progression, for a 13 Hz homeostatic brain wave frequency and a 3 Hz target brain wave frequency, a auditory progression may be generated from 14 Hz to 13 Hz to 12 Hz, followed by subsequent progressions downward by 1 Hz to the final brain wave frequency of 3 Hz, the target brain wave frequency. While a multiple of 1 Hz is disclosed herein, the step up/down amount may be greater or less than this and may be calculated using any/based on any of the factors relating to the listener disclosed in this document. Lastly, and as a result, a desired physiological state of the listener is induced 70 through the resulting activity of the user's brain.

Figure 9:
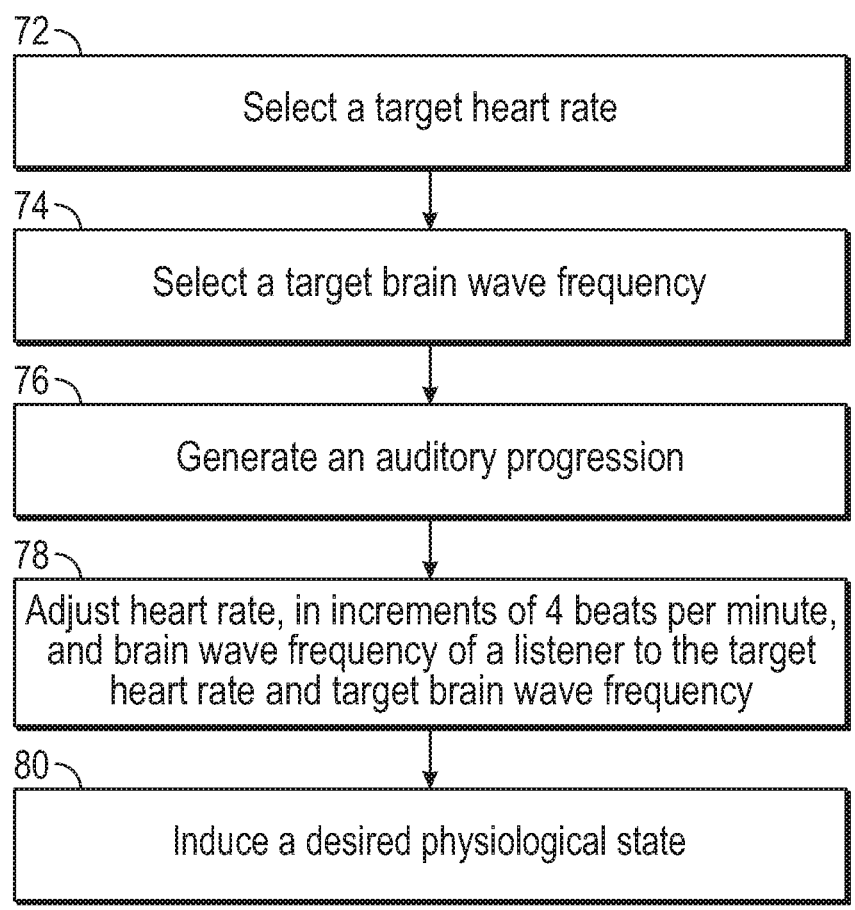
FIG. 9 is a flow chart of an implementation of a method of inducing a desired physiological state, using the auditory progression to adjust a target heart rate, in increments of 4 beats per minute, and adjust a target brain wave frequency.

Referring to FIG. 9, a flow chart of another implementation of a method of inducing a desired physiological state is illustrated. This method implementation uses an auditory progression to adjust a target heart rate, in increments of 4 beats per minute, to adjust a target brain wave frequency. As illustrated, a target heart rate is selected 72. A target brain wave frequency is selected 74. An auditory progression is then generated 76 to be in line with the selected target heart rate and target brain wave frequency. Through exposing the user to the auditory progression through playing a song(s) that include the auditory progression, the heart rate and brain wave frequency of a listener are adjusted to the target values 78 through processing by the listener's brain and interaction of the listener's brain with the central nervous system of the listener.

In particular method implementations, the heart rate may be adjusted in increments of about 4 beats per minute to reach the target heart rate. In various implementations, the target heart rate and target brain wave frequency can be either higher or lower than the homeostatic heart rate and brain wave frequency; or the target heart rate could be lower, while the target brain wave frequency could be higher. In various implementations, the heart rate progression, as laid out in the compilation of songs, may start slightly above or below the homeostatic heart rate, depending on the direction of the desired heart rate change. In various implementations, the starting heart rate for the heart rate progression may be a multiple of 4. In various implementations, if the target heart rate is 76 and the homeostatic heart rate is 95, then the starting beats per minute of the first song of the compilation of songs would be set at either 96 or 100. In various implementations, the beats per minute will then step down, or up, in a progression, in steps of 4 beats per minute to bring the listener to the desired mental state (heart rate being one of the factors of the desired mental state). One implementation of a beats per minute, or heart rate, progression would progress the music of each sequentially played song from 100 to 96 to 92 to 88, and would progress down by 4 beats per minute to a final beats per minute of 76, such that 76 is the target heart rate. While a multiple of 4 beats per minute is disclosed herein, the step up/down amount may be greater or less than this and may be calculated using any/based on any of the factors relating to the listener disclosed in this document. Lastly, and as a result, through processing of the user's brain of the auditory progression, a desired physiological state of the listener is induced 80.

Figure 10:
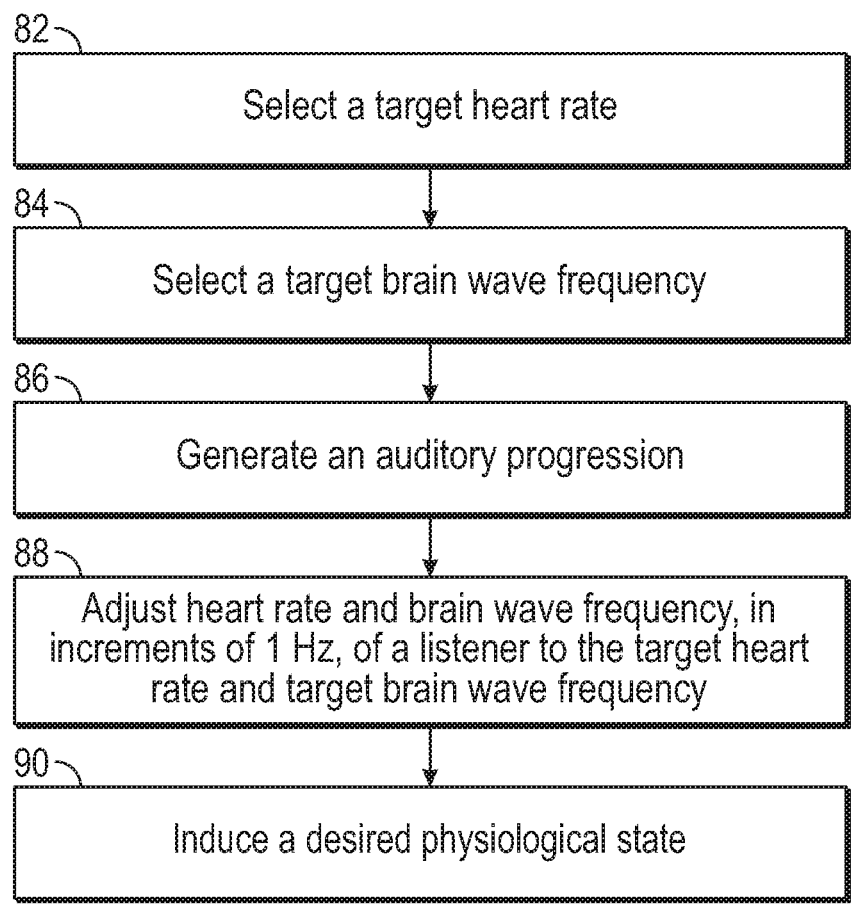
FIG. 10 is a flow chart of an implementation of a method of inducing a desired physiological state, using the auditory progression to adjust a target heart rate and adjust a target brain wave frequency, in increments of 1 Hz.

Referring to FIG. 10, a flow chart of an implementation of a method of inducing a desired physiological state using the auditory progression to adjust a target heart rate and adjust a target brain wave frequency is illustrated. In the implementation illustrated, the brain wave frequency adjustment in increments of 1 Hz is used. As illustrated, a target heart rate is selected 82. A target brain wave frequency is also selected 84. Next, an auditory progression is generated 86 to be in line with the selected target heart rate and target brain wave frequency. Through exposing the listener to the auditory progression by including the auditory progression in one or more songs, the heart rate and brain wave frequency of a listener are adjusted to the target values 88 through processing of the listener's brain. In particular implementations, the brain wave frequency may be adjusted in increments of about 1 Hz to reach the target brain wave frequency. Lastly, and as a result of the processing by the listener's brain working with the listener's central nervous system, a desired physiological state of the listener is induced 90.

Figure 11:
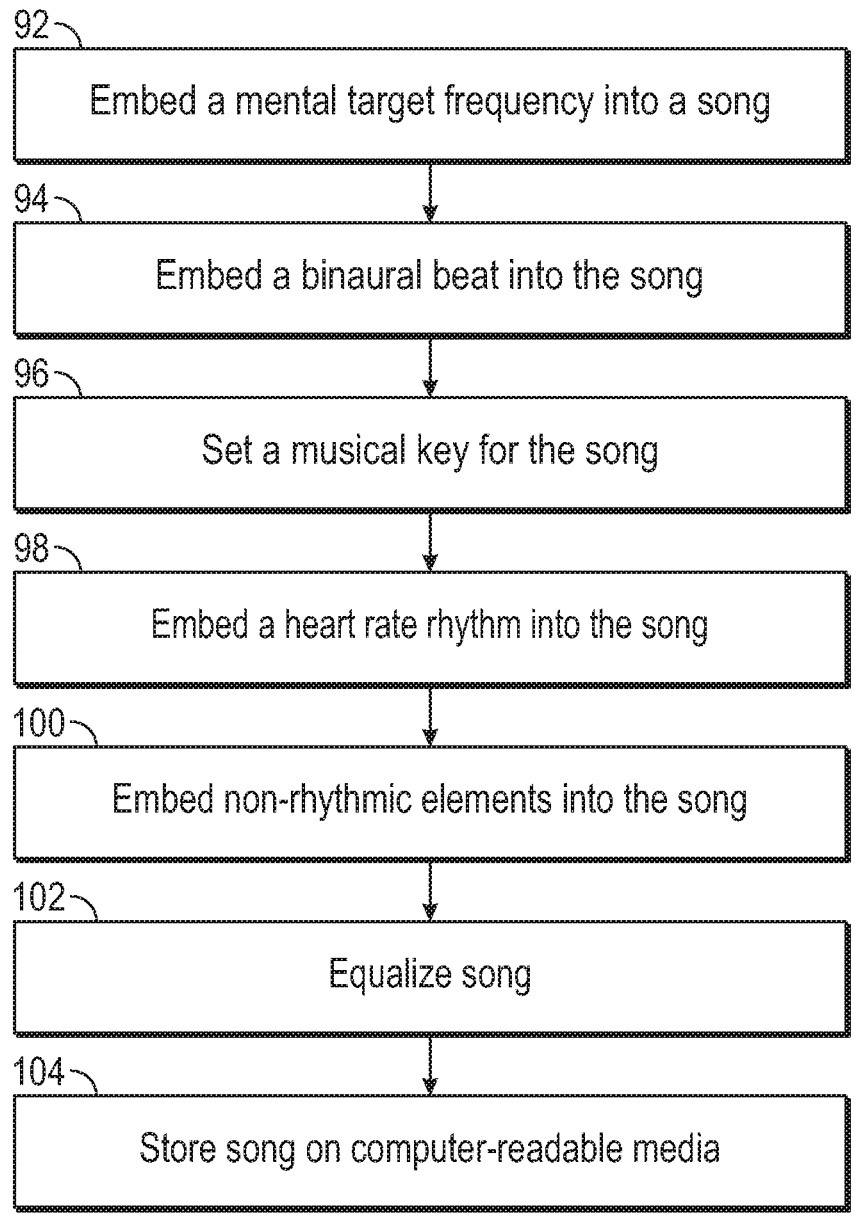
FIG. 11 is a flow chart of an implementation of a method of compiling a song.

Referring to FIG. 11, is a flow chart illustrating an implementation of a method of compiling a song is illustrated. As illustrated, a mental target frequency is embedded into a song 92. The mental target frequency is a particular frequency that may be utilized to help the listener fall asleep, relax, focus, or achieve another desired mental state, and may thus be embedded into the song or compilation of songs. In one implementation, the target mental frequency for falling asleep is 432 Hz through it may be any mental/brain wave frequency disclosed in this document. In one method implementation, the frequency may be embedded/mixed into the track for each song of the compilation of songs at a volume level of about −30 dB root-square-mean (RMS) relative to one or more other frequencies included in the track. As illustrated, a binaural beat is also embedded into track of the song 94. In one implementation, the binaural beat is mixed at a volume of about −30 dB RMS relative to one or more other frequencies included in the track into the track for each song.

A musical key is also set for the song 96. The musical key is determined using a frequency, or mental target frequency, that is one that may help a listener achieve a desired mental state, such as sleep, focus, relaxation, and the like. In various implementations, the mental target frequency likely to reduce anxiety is about 432 Hz, which may induce a sleep state. In various implementations, a relative musical note within the Western musical scale, or a musical note within the equal-tempered scale, may be used. In one implementation, since 432 Hz is not within the standard Western musical scale, the standard tuning is changed, and corresponding musical notes within the relative scale are identified, which produce a correlating major or minor musical note within the Western scale for that correlating musical note. In various implementations, different musical keys may be assigned to one or more songs within the compilation of songs. In various implementations, the musical key of one song will contain the musical key of the compilation of songs within its scale. In one such implementation, if the musical key of the compilation of songs is A, then the musical note A must be in the key and musical mode (Phyrigian, Dorian, Lydian, Myxolydian, by non-limiting example) of each song. In one implementation, the key of each song is the 6th note in the key of the previous song in the sequence of songs. In other various implementations, the 2nd, 3rd, 4th, 5th, or 7th note in the key of the previous song may also be used based on any of the factors relating to the listener disclosed in this document.

As illustrated, a heart rate rhythm is embedded/mixed into the song 98. Non-rhythmic elements are also embedded/mixed into the song 100. In various implementations, the non-rhythmic elements are consistent with the key of the song, but are specifically out of synchronization with the rhythm of the song, and are recorded in a random or pseudo-random fashion using any of a variety of instruments or synthesized sounds. Rhythmic and non-rhythmic elements may be used in combination as a way to confuse the observe-orient-decide-act (OODA) loop of a listener's brain. This confusion of the OODA loop prevents the listener's brain from dismissing/ignoring the music of the song or compilation of songs as being merely repetitive, and may thus force or encourage the brain of the listener to listen to/process the music more intently, in an effort to subconsciously identify a pattern, thus allowing the embedded elements of the song or compilation of songs to have their full effect on the listener's brain waves. In this way, the song engages the listener's brain preventing the listener's mind from wandering away from a focus on the music. In other words, when the listener listens more intently to the music, the brain may absorb more of the embedded frequencies, such as the binaural beats and mental target frequency, which will increase the efficacy of the heart rate rhythm, binaural beat, and mental target frequency progressions on the listener's brain (and correspondingly on the listener's central nervous system). In this way the confusion of the OODA loop via the additional rhythmic and non-rhythmic elements serves to synergistically draw the listener's brain attention into the song, allowing the heart rate rhythm and binaural beat to do their work more efficiently.

As illustrated, the song is equalized 102. Following the mixing/embedding of the various elements of the song, the song is then equalized such that no other frequency may directly interfere with the mental target frequency or binaural beat of each song. Lastly, the song is stored on computer-readable media 104, such as a compact disc (CD), a digital file, or other media accessible to an audio playback device accessible to the listener, in various implementations.

The resulting songs are then provided digitally in a streaming format or recorded on media (CDs, vinyl, flash memory, etc.) for playback to listeners seeking the particular physiological goal of the combination of songs. A wide variety of music data formats may be used to store and process the track information in various implementations.

In places where the description above refers to particular implementations of methods of inducing a desired physiological state and implementing components, sub-components, methods and sub-methods, it should be readily apparent that a number of modifications may be made without departing from the spirit thereof and that these implementations, implementing components, sub-components, methods and sub-methods may be applied to other methods.

What is claimed is:

1. A method of generating an auditory progression for treatment or prophylaxis of a listener afflicted with attention deficit hyperactivity disorder (ADHD), the method comprising:
    selecting a target heart rate for the listener;
        selecting a target brain wave frequency for the listener;
        with the target heart rate and target brain wave frequency for the listener, generating an auditory progression by mixing into a song one or more of a plurality of binaural frequencies calculated from the target heart rate and target brain wave frequency, the auditory progression configured to adjust a heart rate of the listener a heart rate increment toward the target heart rate and to adjust a brain wave frequency of the listener a brain wave increment toward the target brain wave frequency;
        mixing into the song one or more rhythmic and non-rhythmic elements out of synchronization with a rhythm of the song, the one or more rhythmic and non-rhythmic elements configured to confuse the observe-orient-decide-act loop of the listener's brain;
        processing the auditory progression to ensure no other frequencies in the song directly interfere with the adjustment of the heart rate and the adjustment of the brain wave frequency; and
        storing the auditory progression as computer readable instructions on computer readable media for playback to a listener by a playback device comprising a speaker;
        using the computer readable instructions on the computer readable media and the speaker of the playback device to playback the auditory progression;
        while playing the auditory progression, adjusting the heart rate of the listener toward the target heart rate with the heart rate increment of the song; and
        while playing the auditory progression, adjusting the brain wave frequency of the listener toward to the target brain wave frequency with the brain wave increment of the song.

2. The method of claim 1, wherein the auditory progression is composed of a single song.

3. The method of claim 1, wherein the auditory progression is composed of a compilation of songs where each song of the compilation of songs is configured to adjust the heart rate of the listener with the heart rate increment and to adjust a brain wave frequency of the listener with the brain wave increment.

4. The method of claim 1, wherein the target brain wave frequency is 432 Hz.

5. A method of inducing sleep in a listener, the method comprising playing the auditory progression generated by the method of claim 1.

6. A method of generating an auditory progression for treatment or prophylaxis of a listener afflicted with attention deficit hyperactivity disorder (ADHD), the method comprising:
    selecting a target heart rate and a target brain wave frequency for a listener;
    selecting a compilation of songs;
        with the target heart rate, the target brain wave frequency, and the compilation of songs and generating an auditory progression by mixing into each song of the compilation of songs one or more of a plurality of binaural frequencies calculated from the target heart rate and target brain wave frequency, the auditory progression configured to adjust a heart rate of the listener downward to the target heart rate, and to adjust a brain wave frequency of the listener downward to the target brain wave frequency;
        mixing into the song one or more rhythmic and non-rhythmic elements out of synchronization with a rhythm of the song, the one or more rhythmic and non-rhythmic elements configured to confuse the observe-orient-decide-act loop of the listener's brain;
        processing the auditory progression to ensure no other frequencies in each song of the compilation of songs directly interfere with the adjustment of the heart rate and the adjustment of the brain wave frequency;
        storing the auditory progression as computer readable instructions on computer readable media for playback to a listener by a playback device comprising a speaker;
        using the computer readable instructions on the computer readable media and the speaker of the playback device to playback the auditory progression; and
        while playing the auditory progression, adjusting the heart rate of the listener down to the target heart rate with the heart rate increment of each song of the compilation of songs; and
        while playing the auditory progression, adjusting the brain wave frequency of the listener down to the target brain wave frequency with the brain wave increment of each song of the compilation of songs.

7. The method of claim 6, further comprising using the computer readable instructions on the computer readable media and the speaker of the playback device to playback the auditory progression; and inducing a desired physiological state using the auditory progression.

8. The method of claim 6, wherein the target brain wave frequency is 432 Hz.

9. The method of claim 6, further comprising using the computer readable instructions on the computer readable media and the speaker of the playback device to playback the auditory progression; and adjusting the heart rate of the listener in increments of 4 beats per minute until the target heart rate is reached during playback of the auditory progression.

10. The method of claim 6, further comprising using the computer readable instructions on the computer readable media and the speaker of the playback device to playback the auditory progression; and adjusting the brain wave frequency of the listener in increments of 1 Hz until the target brain wave frequency is reached during playback of the auditory progression.

11. A method of inducing sleep in a listener, the method comprising playing the auditory progression generated by the method of claim 6.

\* \* \* \* \*